United States Patent
Kim et al.

(10) Patent No.: US 6,407,264 B2
(45) Date of Patent: Jun. 18, 2002

(54) SYNTHESIS OF ALKYLENE CARBONATES USING A CATALYST SYSTEM COMPRISING METAL HALIDE AND PYRIDINE OR PYRIDINE DERIVATIVE

(75) Inventors: Hoon Sik Kim, Seoul; Jai Jun Kim, Pajoo; Byung Gwon Lee; Hong Gon Kim, both of Seoul, all of (KR)

(73) Assignee: Korea Institute of Science and Technology, Sunkbook-Ku (KR)

( * ) Notice: Subject to any disclaimer, the term of this patent is extended or adjusted under 35 U.S.C. 154(b) by 0 days.

(21) Appl. No.: 09/780,235

(22) Filed: Feb. 9, 2001

(30) Foreign Application Priority Data

Feb. 11, 2000 (KR) .......................................... 2000-6402

(51) Int. Cl.⁷ ........................................... C07D 317/10
(52) U.S. Cl. ....................................................... 549/229
(58) Field of Search ........................................ 549/229

(56) References Cited

U.S. PATENT DOCUMENTS

| | | | |
|---|---|---|---|
| 4,233,221 A | 11/1980 | Raines et al. | 260/340.2 |
| 4,344,881 A | * 8/1982 | Strege et al. | 549/229 |
| 4,353,831 A | * 10/1982 | Strege et al. | 549/229 |
| 5,144,066 A | 9/1992 | Saitou et al. | 562/416 |
| 5,391,767 A | * 2/1995 | Mais et al. | 549/229 |

FOREIGN PATENT DOCUMENTS

| | | | | |
|---|---|---|---|---|
| JP | 59-013776 | 1/1984 | ......... | C07D/317/36 |
| JP | 07-206846 | 8/1995 | ......... | C07D/317/36 |
| JP | 07-206847 | 8/1995 | ......... | C07D/317/36 |
| JP | 09-067365 | 3/1997 | ......... | C07D/317/36 |
| JP | 09-235252 | 9/1997 | ........... | C07C/69/96 |

OTHER PUBLICATIONS

U.S. patent application Ser. No. 09/780,236, filed Feb. 9, 2001.

* cited by examiner

*Primary Examiner*—Floyd D. Higel
*Assistant Examiner*—Golam M. M. Shameem
(74) *Attorney, Agent, or Firm*—Darby & Darby

(57) ABSTRACT

The present invention relates to a method to prepare alkylene carbonate of the formula (1)

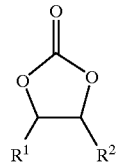

(1)

wherein, $R^1$ and $R^2$ are each independently H; $C_1$–$C_4$ alkyl or phenyl group;

which method characterized by reacting alkylene oxide with carbon dioxide in the presence of a catalyst system comprising a) metal halide [$MX_m$] and b) pyridine or pyridine derivative [Py], wherein Py is selected from a group of pyridines; M is a metal atom selected from the group consisting of Zn, Fe, Mn, Pb and In; X is a halogen selected from the group consisting of Cl, Br and I; and m is 2 or 3.

18 Claims, No Drawings

SYNTHESIS OF ALKYLENE CARBONATES USING A CATALYST SYSTEM COMPRISING METAL HALIDE AND PYRIDINE OR PYRIDINE DERIVATIVE

BACKGROUND OF THE INVENTION

1. Field of the Invention

The present invention relates to a preparation method of an alkylene carbonate by reacting alkylene oxide and carbon dioxide in the presence of a catalyst system comprising metal halide and pyridine or pyridine, derivative.

2. Description of the Background Art

Alkylene carbonates are used in polycarbonate synthesis, as a solvent for polymer electrolyte, an intermediate in pharmaceutical process, an oxyalkylation agent in dyestuff synthesis, a protectant in processing plant and a solvent in textile production process.

Alkylene carbonate has been prepared by reacting carbon dioxide and alkylene oxide in the presence of a catalyst, represented in Scheme 1.

Scheme 1

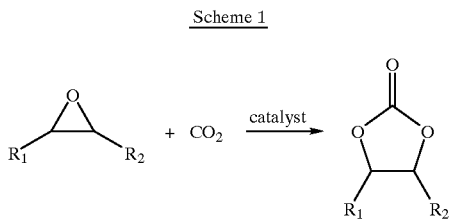

wherein, $R^1$ and $R^2$ are each independently H, $C_1$–$C_4$ alkyl or phenyl group.

In the above reaction, however, there is a limitation that alkylene oxide either decomposes or polymerizes at higher reaction temperatures.

Many catalysts have been developed including inorganic salts, phosphonium halide and ammonium halides. For instance, Japanese Laid-Open Patent No S59-13776 introduced a method of using tetraalkyl halide such as tributyl methyl phosphonium iodide as a catalyst. Japanese Laid-Open Patent No. H9-67365 introduced a method of using KI as a catalyst and Japanese Laid-Open Patent No. H9-235252 describes a method of using polystyrene copolymer containing quatemary phosphonium groups.

These patents claim that the product yield is 50–95% when the reaction is performed at 100–170° C. for 1–5 hours. However, in order to produce alkylene carbonate in high yield, long reaction time and high reaction temperature are required. Also the water content in the raw materials, carbon dioxide and alkylene oxide has to be reduced to than a few hundred ppms.

Japanese Laid-Open Patent No. H7-206846 introduced a method of using an ion change resin substituted with the catalysts such as CsOH, RbOH and ammonium halides. In U.S. Pat. No. 4,233,221, a method of using DOWEX and Amberlite ion exchange resin was reported with a low yield of 30–80% at 80–100° C.

Besides the above-mentioned materials, a phthalocyanine complex containing Co, Cr, Fe, Mn, Ni, Ti, V, or ZR has been used as catalysts. Also in Japanese Laid-Open Patent No. H7-206847, a catalyst system using a heteropolyacid whose hydrogen ion is substituted by Rubidium or Cesium ion was introduced. These two cases, however, require expensive catalysts with low yield of 30–90% at relatively high reaction temperature of 120–180° C.

As mentioned above, the catalysts disclosed in the above arts have one or more problems in terms of activity, reaction condition, cost, water sensitivity, etc.

SUMMARY OF THE INVENTION

Therefore the object of the present invention is to provide a method of producing alkylene carbonate with a high yield in a short reaction time under mild reaction conditions.

As a result of the efforts made to achieve the above aim, the present inventors have found that a catalyst system comprising pyridines and metal halide compounds is more effective than the conventional catalyst system in producing alkylene carbonates by reacting alkylene oxide and carbon dioxide.

DETAILED DESCRIPTION OF THE PREFERRED EMBODIMENTS

The present invention provide a method to prepare alkylene carbonate of the formula (1)

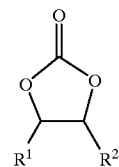

(1)

wherein, each of $R^1$ and $R^2$ is independently H, $C_1$–$C_4$ alkyl or phenyl group;

which method characterized by reacting alkylene oxide with carbon dioxide in the presence of a catalyst system comprising a) metal halide [$MX_m$] and b) pyridine or pyridine derivative [Py], wherein Py is selected from a group of pyridines; M is a metal atom selected from the group consisting of Zn, Fe, Mn, Pb and In; X is a halogen selected from the group consisting of Cl, Br and I; and m is 2 or 3.

The pyridine derivatives include the compounds having the structures of the formulae (2), (3) or (4), and a copolymer between polyvinyl pyridine (PVP) and polyvinyl pyridine

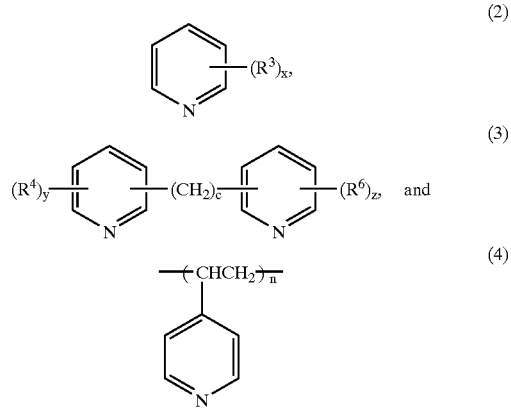

wherein $R^3$, $R^4$ and $R^5$ are each independently H, $C_1$–$C_4$ alkyl or phenyl; each of x, y and z is independently an integer from 0 to 3; and c is an integer from 2 to 4.

The molar ratio of pyridine [Py] to metal halide [$MX_m$] is 10:1~1:5, and more preferably 3:2~1:1.

The amount of metal halide is preferably 0.005~0.1 moles per mole of alkylene oxide. In case the amount of the metal halide used is less than 0.005 mol, reaction becomes too slow. And in case the amount of the catalyst is more than 0.1 mol, the reaction rate and selectivity do not improve any further.

Considering the equipment and operating cost, it is preferable to operate a reaction at a pressure of 10~100 atm.

The reaction temperature is preferably 60~140° C. The reaction proceeds too slow at lower reaction temperature lower than 60° C. When the reaction temperature is too high, alkylene oxide either decomposes or undergoes a self-polymerization reaction and the reaction becomes non-specific.

Although the above reaction could be performed in the absence of the solvent, it is possible to use solvent to prevent excess heat production during the reaction. It is preferable to use alkylene carbonate that is produced from the raw material alkylene oxide as a solvent. For instance, ethylene carbonate is a preferable solvent when ethylene carbonate is synthesized from ethylene oxide and propylene carbonate is preferable when propylene carbonate is synthesized from propylene oxide.

The reaction could be performed by a batch process using the reactor provided with a stirrer or by a continuous process using a bubble column. The invention will be further illustrated by the following examples, but not limited to the examples given.

EXAMPLE 1

A 200 ml high pressure reactor, ethylene oxide (16.80 g, 380 mmol), pyridine (158 mg, 2.0 mmol) and $ZnBr_2$ (223 mg, 1.0 mmol) were charged and pressurized with 10 atm of carbon dioxide. After increasing the temperature to 100° C., carbon dioxide was introduced again up to the pressure of 30 atm During the reaction, carbon dioxide was continuously supplied from a reservoir tank to maintain the pressure to 30 atm.

After the reaction for 1 hour, the volatile components were removed by nitrogen flush and the solid product was separated and weighed to be 31.5 g. The yield was analyzed 93.8% by gas-liquid chromatography.

EXAMPLES 2~8

Alkylene carbonate was synthesized by using different metal halides under identical conditions as in Example 1. The molar ratio of pyridine and metal halides was fixed at 2:1 and the number of moles of the metal halide was set to 1 mmol The results are shown in Table 1.

TABLE 1

| Example | Metal halide compound | Product weight (g) | Yield (%) |
|---|---|---|---|
| 2 | $FeBr_2$ | 27.6 | 82.1 |
| 3 | $FeBr_3$ | 27.0 | 80.3 |
| 4 | $ZnCl_2$ | 17.3 | 51.5 |
| 5 | $ZnI_2$ | 32.4 | 96.4 |
| 6 | $MnBr_2$ | 26.2 | 78.1 |
| 7 | $PbI_2$ | 23.5 | 70.0 |
| 8 | $InCl_3$ | 20.1 | 59.8 |

EXAMPLES 9~16

The process of Example 1 was repeated except that pyridine derivative used in place of pyridine. The results are shown in Table 2.

TABLE 2

| Example | Pyridine compound | Product weight (g) | Yield (%) |
|---|---|---|---|
| 9 | 2-methyl pyridine | 31.3 | 93.2 |
| 10 | 2-ethyl pyridine | 30.9 | 92.0 |
| 11 | 2-propyl pyridine | 29.1 | 86.6 |
| 12 | 2-n-butyl pyridine | 28.8 | 85.8 |
| 13 | 2-phenyl pyridine | 28.6 | 85.3 |
| 14 | 1,2-bis(4-pyridyl) ethane | 31.1 | 92.5 |
| 15 | 1,2-bis(2-pyridyl) ethane | 30.5 | 90.7 |
| 16 | Polyvinylpyridine | 30.9 | 92.0 |

EXAMPLE 17~23

The reaction was performed under the identical conditions as in Example 1 except that the molar ratio of pyridine to $ZnBr_2$ was varied in the range 10:1~1:5. The results are shown in Table 3.

TABLE 3

| Example | a:b | Product weight (g) | Yield (%) |
|---|---|---|---|
| 17 | 10:1 | 28.6 | 85.3 |
| 18 | 5:1 | 31.0 | 92.2 |
| 19 | 2:1 | 31.0 | 92.4 |
| 20 | 1:1 | 31.0 | 92.4 |
| 21 | 1:2 | 30.4 | 90.6 |
| 22 | 1:3 | 30.6 | 91.1 |
| 23 | 1:5 | 29.4 | 87.4 |

EXAMPLE 24~27

The reaction was performed under the identical condition as in Example 1 except that the reaction temperature was varied in the range 60~120° C. The results are in Table 4.

TABLE 4

| Example | Reaction Temperature (° C.) | Product weight (g) | Yield (%) |
|---|---|---|---|
| 24 | 60 | 11.8 | 31.5 |
| 25 | 80 | 29.6 | 88.1 |
| 26 | 100 | 31.0 | 92.4 |
| 27 | 120 | 32.3 | 96.3 |

EXAMPLE 28~30

The reaction was performed under the identical conditions as in Example except that the reaction pressure was varied in the range 20–100 atm. The results are shown in Table 5.

TABLE 5

| Example | Reaction Pressure (atm) | Product weight (g) | Yield (%) |
|---|---|---|---|
| 28 | 20 | 30.0 | 90.2 |
| 29 | 50 | 31.2 | 92.9 |
| 30 | 100 | 32.0 | 95.3 |

EXAMPLE 31~34

The reaction was performed under the identical condition as in Example 1 except that the molar ratio of $ZnBr_2$ to ethylene oxide was varied in the range 0 0005~0.1. The molar ratio of pyridine/$ZnBr_2$ and the amount of ethylene oxide were fixed as 2:1 and 16, 80 g (380 mmol), respectively The results are shown in Table 6.

TABLE 6

| Example | ZnBr$_2$/ethylene oxide (mole ratio) | Product weight (g) | Yield (%) |
|---|---|---|---|
| 31 | 0.0005 | 23.5 | 70.1 |
| 32 | 0.001 | 31.0 | 92.2 |
| 33 | 0.01 | 32.9 | 98.1 |
| 34 | 0.1 | 33.3 | 99.2 |

EXAMPLE 35~38

The reaction was performed under the identical condition as in Example 1 except that different kind of alkylene oxide was used. The result are shown in Table 7.

TABLE 7

| Example | Alkylene oxide | Product weight (g) | Yield (%) |
|---|---|---|---|
| 35 | Propylene oxide | 36.3 | 93.5 |
| 36 | 2-methyl-1,2-epoxy propane | 39.4 | 88.7 |
| 37 | 2,3-epoxy butane | 38.9 | 87.6 |
| 38 | Styrene oxide | 56.6 | 90.8 |

EXAMPLE 39~40

The reaction were performed under the identical condition as in Example 1 except that ethylene carbonate or propylene carbonate was used as a solvent. The amount of the solvent used was 200% of ethylene oxide by weight. The results are shown in Table 8.

TABLE 8

| Example | Solvent | Product weight (g) | Yield (%) |
|---|---|---|---|
| 39 | Ethylene carbonate | 30.9 | 92.1 |
| 40 | Propylene carbonate | 30.9 | 91.9 |

According to the present invention, alkylene carbonates can be synthesized in high yield under a mild reaction condition. The catalyst of the present invention has several advantages in terms of economical point of view because it is inexpensive, highly active and reusable.

As the present invention may be embodied in several forms without departing from the spirit or essential characteristics thereof, it should also be understood that the above-described embodiments are not limited by any of the details of the foregoing description, unless otherwise specified, but rather should be construed broadly within its spirit and scope as defined in the appended claims, and therefore all changes and modifications that fall within the meets and bounds of the claims, or equivalence of such meets and bounds are therefore intended to be embraced by the appended claims.

What is claimed is:

1. A method to prepare alkylene carbonate of the formula (1)

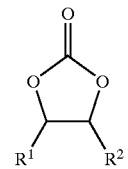

wherein, $R_1$ and $R_2$ are each independently H, $C_1$–$C_4$ alkyl or a phenyl group; comprising reacting alkylene oxide with carbon dioxide in the presence of a catalyst comprising a) metal halide [MX$_m$] and b) pyridine or pyridine derivative [Py], wherein Py is selected from a group of pyridines; M is a metal atom selected from the group consisting of Zn, Fe, Mn, Pb and In; X is a halogen selected from the group consisting of Cl, Br, and I; and m is 2 or 3.

2. The method according to claim 1, wherein the pyridine ligand Py has a structure selected from the group consisting of the formulae (2), (3) and (4)

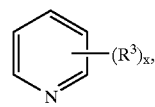

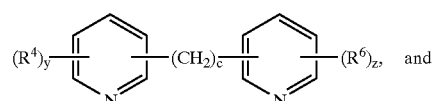

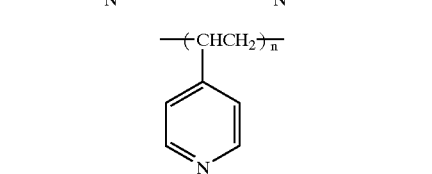

wherein $R^3$, $R^4$ and $R^5$ are each independently H, $C_1$–$C_4$ alkyl or phenyl; each of x, y and z is independently an integer from 0 to 3; and c is an integer from 2 to 4.

3. The method according to claim 1, wherein the molar ratio of [Py] to [MX$_m$] is 10:1~1:5.

4. The method according to claim 2, wherein the molar ratio of [Py] to [MX$_m$] is 10:1~1:5.

5. The method according to claim 3, wherein the molar ratio of [Py] to [MX$_m$] is 3:2~1:1.

6. The method according to claim 4, wherein the mole ratio of [Py] to [MX$_m$] is 3:2~1:1.

7. The method according to claim 1, wherein the molar ratio of the catalyst to alkylene oxide is 0.0005~0.1:1.

8. The method according to claim 2, wherein the molar ratio of the catalyst to alkylene oxide is 0.0005~0.1:1.

9. The method according to claim 1, wherein the reaction temperature is 60~140° C.

10. The method according to claim 2, wherein the reaction temperature is 60~140° C.

11. The method according to claim 1, wherein the reaction pressure Is 10~100 atm.

12. The method according to claim 2, wherein the reaction pressure is 10~100 atm.

13. The method according to claim 1, wherein solvent is not used in the reaction.

14. The method according to claim 2, wherein solvent is not used in the reaction.

15. The method according to claim 1, wherein the identical material to the produced alkylene carbonate is used as a solvent.

16. The method according to claim 2, wherein the identical material to the produced alkylene carbonate is used as a solvent.

17. The method according to claim 15, wherein the solvent is selected from ethylene carbonate and propylene carbonate.

18. The method according to claim 16, wherein the solvent is selected from ethylene carbonate and propylene carbonate.

* * * * *